(12) United States Patent
Lancaster et al.

(10) Patent No.: US 9,063,143 B2
(45) Date of Patent: *Jun. 23, 2015

(54) CANCER PLATINUM RESISTANCE DETECTION AND SENSITIZATION METHOD

(75) Inventors: Johnathan Lancaster, Tampa, FL (US); Douglas C. Marchion, Seminole, FL (US); Dung-Tsa Chen, Tampa, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 187 days.

This patent is subject to a terminal disclaimer.

(21) Appl. No.: 12/975,970

(22) Filed: Dec. 22, 2010

(65) Prior Publication Data

US 2011/0166095 A1 Jul. 7, 2011

Related U.S. Application Data

(63) Continuation of application No. PCT/US2009/003863, filed on Jun. 26, 2009.

(60) Provisional application No. 61/075,987, filed on Jun. 26, 2008.

(51) Int. Cl.
*G01N 33/53* (2006.01)
*G01N 33/574* (2006.01)

(52) U.S. Cl.
CPC .... *G01N 33/57449* (2013.01); *G01N 33/57484* (2013.01); *G01N 2800/52* (2013.01)

(58) Field of Classification Search
CPC .............................................. G01N 33/57449
See application file for complete search history.

(56) References Cited

U.S. PATENT DOCUMENTS

| | | | |
|---|---|---|---|
| 4,474,893 | A | 10/1984 | Reading |
| 4,676,980 | A | 6/1987 | Segal et al. |
| 4,816,567 | A | 3/1989 | Cabilly et al. |
| 5,675,063 | A | 10/1997 | Knight |
| 6,130,201 | A | 10/2000 | Croce et al. |
| 2004/0229843 | A1 | 11/2004 | Toole et al. |
| 2007/0254295 | A1 | 11/2007 | Harvey et al. |

OTHER PUBLICATIONS

Lizcano et al, Biochem. J. 349:547-557, 2000.*
Hayakawa et al, Cancer Res 60:5988-5994, 2000.*
Nicholson et al Breast Cancer Research and Treatment 81:117-128, 2003.*
GenBank No. Q92934 2012, Bad Sequence 2012.*
Gilmore, Andrew P. et al. Activation of BAD by Therapeutic Inhibition of Epidermal Growth Factor Receptor and Transactivation by Insulin-like Growth Factor Receptor. Journal of Biological Chemistry, vol. 277, No. 31, Aug. 2, 2002. pp. 27643-27650.

Anderson, Neil G. et al. ZD1839 (Iressa), A Novel Epidermal Growth Factor Receptor (EFGR) Tyrosine Kinase Inhibitor, Potently Inhibits the Growth of EGFR-Postive Cancer Cell Lines With or Without ERBB2 Overexpression. International Journal of Cancer, vol. 94, No. 6, Dec. 15, 2001. pp. 774-782.
Hayakawa, Jun et al. Inhibition of Bad Phosphorylation Either at Serine 112 via Extracellular Signal-related Protein Kinase Cascade or at Serine 136 via Akt Cascade Sensitizes Human Ovarian Cancer Cells to Cisplatin. Cancer Research, vol. 60, No. 21, Nov. 1, 2000. pp. 5988-5994.
Zhou, Xiao-Mai et al. Growth Factors Inactivate the Cell Death Promoter BAD by Phosphorylation of Its BH3 Domain on Ser155. The Journal of Biological Chemistry, Aug. 11, 2000. pp. 25046-25051.
Lopiccolo, Jaclyn et al. Targeting the PI3K/Akt/mTOR Pathway: Effective Combinations and Clinical Considerations. Drug Resistance Updates, vol. 11, No. 1-2, Feb. 1, 2008. pp. 32-50.
Marchion, Douglas C. et al. BAD Phosphorylation Determines Ovarian Cancer Chemosensitivity and Patient Survival. Clinical Cancer Research, vol. 17, No. 19, Oct. 1, 2011. pp. 6356-6366.
Abstracts presented for the 41st Annual Meeting of the Society of Gynecologic Oncologists. Gynecologic Oncology, vol. 116, No. 3, Mar. 1, 2010. pp. S2-S169.
Extended European Search Report pursuant to Rule 62 EPC issued Feb. 3, 2012 for European Patent Application No. 09770577.6-2404.
International Search Report for PCT/US2009/003863 dated Feb. 17, 2010.
Lizcano et al., Regulation of BAD by cAMP-dependent Protein Kinase is Mediated Via Phosphorylation of a Novel Site, Ser155, Biochem. J., 2000, vol. 349, pp. 547-557.
Morrison et al., Chimeric Human Antibody Molecules: Mouse Antigen-Binding Domains with Human Constant Region Domains, Proc. Natl. Acad. Sci., USA, 1984, vol. 81, pp. 6851-6855.
Steplewski et al., Isolation and Characterization of Anti-Monosialoganglioside Monoclonal Antibody 19-9 Class-Switch Variants, Proc. Natl. Acad. Sci., USA, 1985, vol. 82, pp. 8653-8657.
Mullinax et al., Identification of Human Antibody Fragment Clones Specific for Tetanus Toxoid in a Bacteriophage Lambda Immunoexpression Library, Proc. Natl. Acad. Sci., USA, 1990, vol. 87, pp. 8095-8099.
Jetzt et al., Adenoviral-Mediated Expression of a Kinase-Dead Mutant of Akt Induces Apoptosis Selectively in Tumor Cells and Suppresses Tumor Growth in Mice, Cancer Research, 2003, vol. 63, pp. 6697-6706.

(Continued)

*Primary Examiner* — Lei Yao

(74) *Attorney, Agent, or Firm* — Robert J. Varkonyi; Smith & Hopen, P.A.

(57) ABSTRACT

The phosphorylation status of the BAD protein is a determinant of ovarian cancer cell responsiveness to platinum chemotherapy. Indirect manipulation of BAD phosphorylation status influences cisplatin sensitivity. BAD phosphorylation represents a biomarker that predicts platinum sensitivity and is a therapeutic target to increase platinum sensitivity. The methods employ phospho-specific antibody against a particular amino acid residue or site. Phospho-specific protein characterization methods include immunohistochemical (IHC), flow cytometric, immunofluorescent, capture-and-detection, or reversed phase assay.

9 Claims, 12 Drawing Sheets

(56) References Cited

OTHER PUBLICATIONS

Muslin et al., Interaction of 14-3-3 with Signaling Proteins is Mediated by the Recognition of Phosphoserine, Cell, 1996, vol. 84, pp. 889-897.
Kohler et al., Derivation of Specific Antibody-Producing Tissue Culture and Tumor Lines by Cell Fusion, Eur. J. Immunol., 1976, vol. 6, pp. 511-519.
Merrifield, Solid Phase Peptide Synthesis. I. The Synthesis of a Tetrapeptide, Am. Chem. Soc., 1963, vol. 85, pp. 2149-2154.
Hong et al., Antisense Bcl2 Oligonucleotide in Cisplatin-Resistant Bladder Cancer Cells, BJU International, 2002, vol. 90, pp. 113-117.
Huse et al., Generation of a Large Combinatorial Library of the Immunoglobulin Repertoire in Phage Lambda, Science, 1989, vol. 246, pp. 1275-1281.
Chittenden et al., A Conserved Domain in Bak, Distinct from BH1 and BH2, Mediates Cell Death and Protein Binding Functions, The EMBO Journal, 1995, vol. 14, No. 22, pp. 5589-5596.
Cheng et al., AKT Signal Transduction Pathway in Oncogenesis, Encyclopedic Reference of Cancer, Berlin Heidelberg and New York: Springer, 2001, pp. 35-37.
Boyd et al., Bik, a Novel Death-Inducing Protein Shares a Distinct Sequence Motif with Bcl-2 Family Proteins and Interacts with Viral and Cellular Survival-Promoting Proteins, Oncogene, 1995, vol. 11, pp. 1921-1928.
Oltvai et al., Checkpoints of Dueling Dimers Foil Death Wishes, Cell, 1994, vol. 79, pp. 189-192.
Spira et al., The Identification of Monoclonal Class Switch Variants by Sib Selection and an ELISA Assay, Journal of Immunological Methods, 1984, vol. 74, pp. 307-315.
Walker et al., Interaction of Human IgG Chimeric Antibodies with the Human FcRl and FcRll Receptors: Requirements for Antibody-Mediated Host Cell-Target Cell Interaction, Molecular Immunology, 1989, vol. 26, No. 4, pp. 403-411.
Zhang et al., Reliability of Tissue Microarrays in Detecting Protein Expression and Gene Amplification in Breast Cancer, Mod. Pathol., 2003, vol. 16, No. 1, pp. 79-85.
Antibodies: A Laboratory Manual, Chapter 5, pp. 75-76, Harlow & Lane Eds., Cold Spring Harbor Laboratory, 1988.
Kohler et al., Continuous Cultures of Fused Cells Secreting Antibody of Predefined Specificity, Nature, 1975, vol. 256, pp. 495-497.
Czernik et al., Production of Phosphorylation State-Specific Antibodies, Methods in Enzymology, 1991, vol. 201, pp. 264-283.
Yin et al., BH1 and BH2 Domains of Bcl-2 are Required for Inhibition of Apoptosis and Heterodimerization with Bax, Nature, 1994, vol. 369, pp. 321-323.
Tan, Y., Demeter, M. R., Ruan, H., Comb, M. J., BAD Ser-155 Phosphorylation Regulates BAD/Bcl-XL Interaction and Cell Survival. The Journal of Biological Chemistry, vol. 275, No. 33, Issue of Aug. 18, 2000, pp. 25865-25869.
Cell Signaling Technology, Material Safety Data Sheet (MSDS) for H-89, Dihydrochloride. www.cellsignal.com. Accessed on Jan. 11, 2013.
Akt blocks ligand binding and protects against expanded polyglutamine androgen receptor toxicity. Hum. Mol. Genet., Jul. 1, 2007. vol. 16, No. 13. pp. 1593-1603. hmg.oxfordjournals.org/content/16/13/1593/F7.expansion. Accessed on Dec. 4, 2012.
Cell Signaling Techology, PD98059 (MEK1 Inhibitor). www.cellsignal.com. Accessed on Jan. 11, 2013.
Alessi, Dr. The Protein kinase C inhibitors Ro 318220 and GF 109203X are equally potent inhibitors of MAPKAP kinase-1beta (Rsk-2) abd p70 S6 kinase. FEBS Lett. Feb 3, 1997; 402(2-3);121-3. http://www.ncbi.nlm.nih.gov/pubmed/9037179. Accessed on Dec. 3, 2012.
Cell Signaling Technology, Product Pathways—MAPK signaling. http://www.cellsignal.com/products/9903.html. Accessed on Dec. 3, 2012.
Cell Signaling Technology, Product Pathways—PI3K / Akt Signaling. http://www.cellsignal.com/products/9951.html. Accessed on Dec. 3, 2012.

\* cited by examiner

US 9,063,143 B2

CANCER PLATINUM RESISTANCE DETECTION AND SENSITIZATION METHOD

CROSS REFERENCE TO RELATED APPLICATIONS

This application is a continuation of prior filed International Application, Serial Number PCT/US2009/003863 filed Jun. 26, 2009, which claims priority to U.S. provisional patent application No. 61/075,987, entitled "Cancer Platinum Resistance Detection and Sensitization Method", filed Jun. 26, 2008 which is hereby incorporated by reference into this disclosure.

STATEMENT OF GOVERNMENT INTEREST

This invention was made with Government support under Grant No. W81XWH-08-2-0101 awarded by the Department of Defense (ARMY/MRMC). The Government has certain rights in the invention.

FIELD OF INVENTION

This invention relates to cancer resistance determination and sensitization. Specifically, the invention provides BAD protein phosphorylation status and manipulation indicate cancer responsiveness to platinum chemotherapy.

BACKGROUND OF INVENTION

The biologic basis to the evolution of platinum resistance has been attributed to changes in many cellular functions including drug efflux, glutathione levels, and DNA repair capacity. However, a comprehensive understanding of the global molecular changes that accompany the development of platinum-resistance in ovarian cancer cells has not yet been elucidated. Current technologies cannot efficiently determine the potential therapeutic response of a cancer prior to treatment. Platinum compounds are chemotherapeutic agents effective in treatment of many human solid tumors. Response to platinum-based chemotherapy is one of the most critical determinants of outcome for patients with advanced stage epithelial ovarian cancer. Currently the standard treatment protocol used in the initial management of such patients is primary cytoreductive surgery, followed by adjuvant therapy with a platinum and taxane. Approximately 70% of patients will have a complete clinical response to this initial therapy, with absence of clinically detectable residual disease on clinical examination, radiologic imaging, or serum CA125 tumor marker. However, for most patients, remission is short-lived, and the majority will develop recurrent disease that ultimately becomes resistant to further platinum therapy, resulting in extremely poor survival.

The BCL-2 family of proteins govern mitochondrial outer membrane permeabilization and constitute an intracellular checkpoint of apoptosis, largely defined by conserved motifs termed BCL-homology regions. (Yin et al, *Nature* 369:321-323, 1994 which is incorporated by reference). The BCL-homology regions 1, 2, 3 and 4 (BH1 through BH4) domains have been shown crucial for function (Yin et al. *Nature* 369: 321-20 323, 1994 which is incorporated by reference; Boyd et al., *Oncogene* 11:1921-1928; Chittenden et al., *Embo J* 14:5589-5596, 60 1995 which are incorporated by reference). Members of the BCL-2 family typically can competitively heterodimerize and homodimerize, determining whether a cell will respond to an apoptotic signal (Oltvai and Korsmeyer, *Cell* 79:189-192, 1994 which is incorporated by reference).

BAD (BCL-2 Associated Death Promotor) is a proapoptotic Bcl-2 family protein that regulates the intrinsic apoptosis pathway. In its transient state, BAD is phosphorylated, rendering the protein inactive. Phosphorylated BAD interacts with 14-3-3 scaffold proteins in the cytoplasm, until cleavage by caspase-3 or dephosphorylation by calcineurin allows the release of BAD. 14-3-3 binding has been shown to be sequence-specific to a phosphoserine containing motif (Muslin et al. *Cell* 84:889-896, 1996 which is incorporated by reference), based on phosphorylation of serine residues (Serine-259 and Serine-621) in Raf-1. Once BAD is dephosphorylated (posttranslational modification), it is active; it translocates from the cytosol to the mitochondria and forms heterodimers with BCL proteins to block the antiapoptotic functions of the proteins.

Current technology does not monitor cellular phosphorylation status to determine the potential for platinum therapy resistance. Accordingly, there is an unmet need to develop screening systems to aid in the analysis and prognosis of current and possible future therapy resistance.

SUMMARY OF INVENTION

Many genes associated with BAD phosphorylation status demonstrate increased or decreased expression as cisplatin resistance increased with serial cisplatin in-vitro treatments. Many of these genes also show increased or decreased expression associated with CR (platinum sensitivity) versus IR (platinum resistance) in patient samples. PP2C and Bcl2 expression decreased with increasing cisplatin resistance in cell lines. Conversely, CDK1, 14-3-3, and JNK1, AKT expression increased with increasing cisplatin resistance in cell lines. Further, PP2C AKT, and p90RSK decreased in IR (platinum resistant) patient samples.

Phospho-BAD protein expression was found to increase, using IHC, as ovarian cancer cell lines became more resistant to platinum with serial in-vitro and contained higher expression in platinum resistant versus platinum sensitive cells. As expected, phospho-BAD protein expression was higher in IR (platinum resistant) patient samples versus CR (platinum sensitive). Inhibition of AKT by triciribine resulted in a decrease in cell survival (measured by MTT assay), and increased in ovarian cancer cell platinum sensitivity.

The phosphorylation status of the BAD protein is a determinant of ovarian cancer cell responsiveness to platinum chemotherapy and represents a biomarker that predicts platinum sensitivity. Indirect manipulation of BAD phosphorylation status is accomplished, for example, by inhibiting AKT pathway phosphorylation of BAD by TCN inhibition or siRNA gene knockdown, or by increasing BAD phosphorylation using siRNA to PPLC. BAD phosphatase levels influence cisplatin sensitivity and can be used as a therapeutic target to increase platinum sensitivity.

The methods and kits of the invention may employ virtually any phospho-specific antibody capable of detecting a desired signal transduction protein when phosphorylated at a particular residue or site. Phospho-specific antibodies are widely commercially available (e.g. from Cell Signaling Technology, Inc.; BioSource, Inc.; Santa Cruz Biotechnology, Inc.; Upstate Biotechnology, Inc.), and may also be produced by techniques in the art. In the methods and kits for identifying protein biomarkers, panels of one or more phospho-specific antibodies are employed, such as the use of two or more phospho-specific antibodies to detect the phosphorylation statuses of at least one phosphorylation site on the BAD protein. A single phospho-specific antibody (polyclonal or monoclonal) may be used to detect the phosphorylation status of a single correlated amino acid residue, for example, if only one such residue has been identified as relevant to the disease for which therapy is being considered. Alternatively, two or more phospho-specific antibodies against two or more correlated residues may be used. The particular number of antibodies selected for predicting patient response in a given case will depend on the number of amino acid residues that have been identified as relevant, correlated to patient responsiveness to the particular therapeutic composition in a particular disease. One or multiple biomarkers may be identified as relevant predictors of patient response to a particular therapeutic composition for a particular disease. For example, Serine 155 phosphorylation status may be probed to determine cisplatin responsiveness, as discussed below.

In certain embodiments, control antibodies may also be included which do not detect phosphorylation status. For example, protein-specific antibodies that detect merely the presence of a given signal transduction protein (not its modification status), or site-specific antibodies that detect a target in its unphosphorylated form. Phospho-specific antibodies may be use to detect phosphorylation of correlated resides in the examined cellular sample sequentially, in tandem, or simultaneously to detect activation statuses of the various targets.

In still another embodiment, the invention provides a kit for identifying protein biomarkers of disease outcome or patient responsiveness to a therapeutic composition having efficacy against a disease involving altered signal transduction, comprising (a) a panel of phospho-specific antibodies against a plurality of signal transduction proteins, and (b) one or more additional reagent(s) suitable for detecting binding of the antibodies to said signal transduction pro-tein(s) in a cellular assay. In a certain embodiments of these kits, the cellular assay comprises an immunohistochemical (IHC), flow cytometric, immunofluorescent, capture-and-detection, or reversed phase assay, and the kit is optimized for staining or analyzing at least one cellular sample from a patient. In other preferred embodiments, the kit comprises phospho-specific antibodies against one or more residues of BAD.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
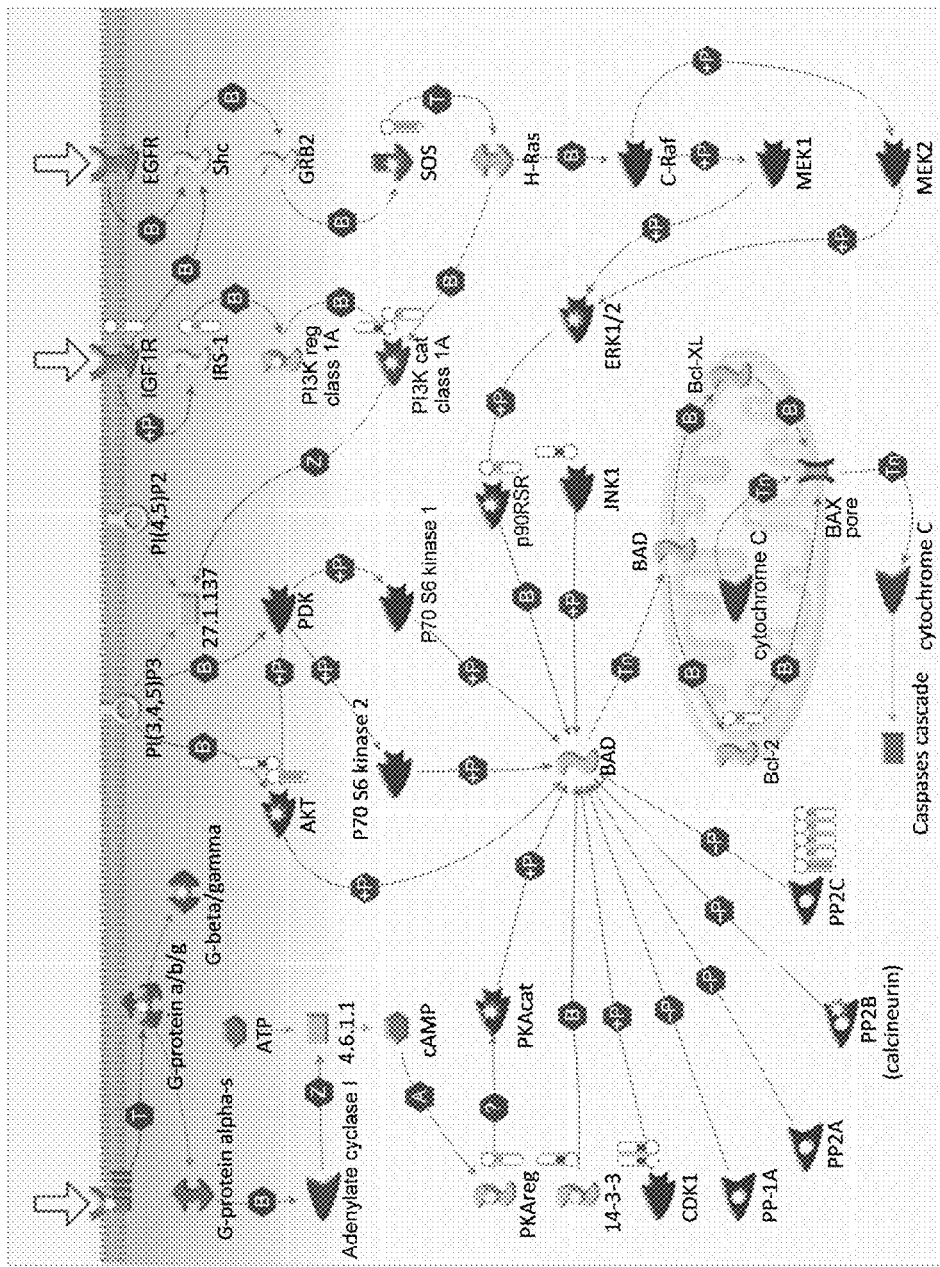
FIG. 1 depicts the genes associated with BAD phosphorylation status whose expression is affected by cisplatin resistance.
Figure 2:
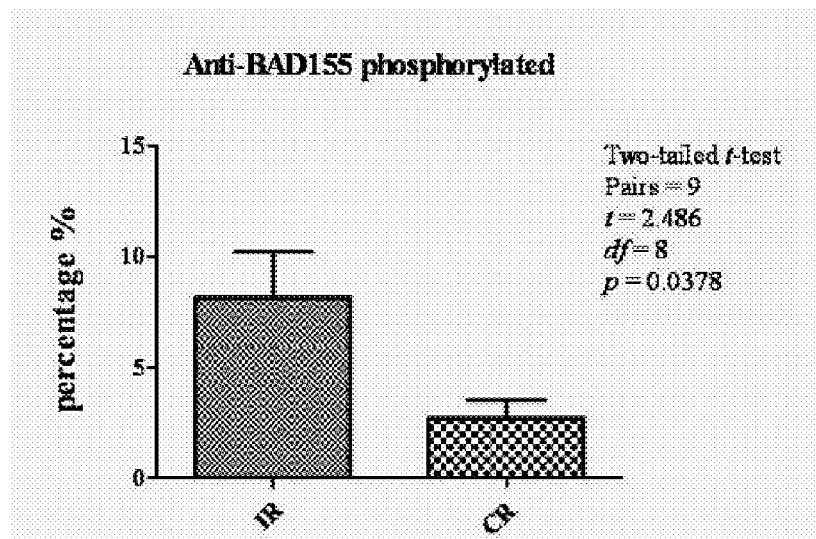
FIG. 2 depicts BAD phosphorylation levels for IR (platinum resistant) and CR (platinum sensitive) patient samples.

The term "antibody" or "antibodies" refers to all types of immunoglobulins, including IgG, IgM, IgA, IgD, and IgE, including Fab or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol* 26: 403-11 (1989); Morrision et al., *Proc. Nat'l. Acad. Sci.* 81: 6851 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.) Polyclonal antibodies useful in the practice of the methods and kits of the invention may be produced according to standard techniques by immunizing a suitable animal (e.g., rabbit, goat, etc.) with an antigen encompassing the phosphorylated residue or site to which specificity is desired, collecting immune serum from the animal, separating the polyclonal antibodies from the immune serum, and screening for phospho-epitope specificity in accordance with known procedures. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85: 21-49 (1962)) Monoclonal antibodies suitable for use in the methods and kits of the invention may be produced in a hybridoma cell line according to the well-known technique of Kohler and Milstein. (*Nature* 265: 495-97 (1975); Kohler and Milstein, *Eur. J. Immunol.* 6: 511 (1976)). Monoclonal antibodies so produced are highly specific, and improve the selectivity and specificity of the therapeutic-response predictive and methods provided by the invention. For example, a solution containing the appropriate antigen (i.e. a desired phospho-epitope of a signal transduction protein) may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997). Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)).

As used herein, the term "BAD" or "Bad" refers to the mammalian BAD gene and mammalian BAD proteins, including isoforms thereof, unless otherwise identified.

The term "BAD native protein" and full-length BAD protein" as used herein refers to a full length BAD polypeptide of 204 amino acids, or as naturally occurs in a mammalian species, such as human, mouse, primate, etc. A preferred BAD native protein is a polypeptide corresponding to the amino acid sequence shown in FIG. 1. A native BAD protein is also one present in naturally-occurring somatic cells which express the BAD gene.

As used herein, the term "cancer" or "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

The term "fragment" as used herein refers to a polypeptide that has an amino-terminal and/or carboxy-terminal deletion, but where the remaining amino acid sequence is identical to the corresponding positions in the sequence deduced from a full-length cDNA sequence.

The term "analog", "mutein" or "mutant" as used herein is a polypeptide which is comprised of a segment of at least 10 amino acids that possess substantial identity to a potion of the naturally occurring protein. For example, a BAD analog comprises a segment of at least 10 amino acids that has substantial identify to a BAD protein, such as the BAD protein of FIG. 1. In an embodiment, the BAD analog has at least one property enabling it to bind to BCL-2 or bind to BCL-X under suitable conditions. The analog typically comprises a conservative amino acid substitution, deletion, or addition, with respect to the naturally occurring protein. Some analogs may lack activity, but still be useful in the present invention.

The term "BAD polypeptide" is used herein to refer to a BAD native protein, fragment, or analog of BAD, or a fusion event between BAD and another polypeptide. Also included are artificial polypeptide sequences substantially identical to a native protein, fragment or analog of BAD, such as a polypeptide string generated from BAD cDNA.

The term "label" or "labels" as used herein refer to incorporation of a detectable marker, such as by incorporation of a radiolabeled amino acid, or biotinylated amino acid that can be detected by marked avidin, including streptavidin, or be detected by other optical or calorimetric methods. Various labeling methods or polypeptides and glycoproteins are known in the art, including radioisotope labeling, such as 3H, 14C, 35Sm 125I) or fluorescent labeling, like horseradish peroxidase). Other methods are known in the art and may also be used in conjunction with or in replacement of the examples.

The term "significant correlation" with respect to a biomarker residue means the biomarker (or a set of biomarkers) the activity of which, when compared to and correlated with an outcome, such as patient response to a therapy or patient prognosis, is statistically different than what would be predicted by chance alone; in the exemplary case of Chi-Squared tests calculations, the statistic characterizes whether the observed distribution of frequencies in a sub-population is significantly different than the overall distribution of frequencies observed in the entire population; the P value that is generally accepted to be statistically relevant is below 0.05, which translates into a confidence level of 95% that the observations are not due to chance alone, and that the correlation is thus significant.

Cellular samples to be analyzed in the method of the invention may consist of tissue samples taken during the course of surgery, biopsies taken for the sake of patient diagnosis, ductal lavages, fine needle aspirants, blood, serum, lymphatic, urine, ascites fluid, or other fluid samples or skin, bone marrow sample, hair follicle or scrapings taken for clinical analysis. The cells may also be derived as cell smears in which fresh or fixed cells are placed on slides. Suitable cellular samples from a subject (i.e. biological samples comprising at least one cell or its protein contents) include tissue or tumor samples, from individual or multiple cell samples. Fresh samples may be analyzed by immunohistochemical or immunofluorescent methods on whole cells or by reverse-phase array methods on lysates prepared from the patient samples. Tissue samples may be dispersed, enabling a flow cytometric analysis. Alternatively, the samples may be frozen or fixed using fixation methods well known in the art as described below in the examples. The fixed cells may be paraffin-embedded or used in flow cytometric analyses.

The analysis of the tissue or cell samples may be done by standard immunohistochemical methods well known in the art as described in the examples. This analysis may be done manually or by automatic cell staining instruments. The detection of the bound antibodies may be done with solid substrates or with fluorescent labels. Scoring of the stained tissues or cells may be done manually or by automatic analysis. The fixed cells may be analyzed by flow cytometry using multiple antibodies following standard methods well known in the art.

In certain embodiments of the invention, the cellular sample will be a tumor sample from a cancer patient. In other embodiments, multiple tissue samples are prepared as a tissue microarray for IHC-based staining and analysis. Construction of tissue microarrays is well known in the art (Zhang D. et al. Mod Pathol (2003) January; 16(1):79-85).

Phosphorylation status(es) in a cellular sample are examined, in accordance with the methods and kits of the invention, using phospho-specific antibodies in a cellular assay, namely, any assay suitable for detecting in vivo protein activity in a particular cell. Examples of suitable cellular assays include the following assays: immunohistochemistry (IHC), flow cytometry (FC), immunofluorescence (IF) (all of which are whole cell or tissue-based staining assays), and capture-and-detection (e.g. ELISA), or reversed phase assays (which are cell-lysate based assays). Protein localization, which plays a significant role in protein function, within a cell may also be determined, in addition to phosphorylation status. Reagents suitable for detecting binding of the antibodies may, for example, be a second antibody conjugated to a detectable group or label. The kit may include an appropriate assay container, for example, a microtiter plate, slide, etc. The reagents may also include ancillary agents such as buffering agents and protein stabilizing agents, e.g., polysaccharides and the like. The kit may further include, other agents necessary for signal detection, such as blocking agents for reducing background interference in a test, control reagents, apparatus for conducting a test, and the like.

The following Examples are provided only to further illustrate the invention, and are not intended to limit its scope, except as provided in the claims appended hereto. The present invention encompasses modifications and variations of the methods taught herein which would be obvious to one of ordinary skill in the art.

Example 1

Identification of Breast and Prostate Cancer Biomarkers Using IHC-Based Analysis Ovarian cancer cell lines (C13, OV2008, A2780S, A2780CP, IGROV1, T8, A2008, IOSER, and OVCAR5) were grown in RPMI-1640 supplemented with 10% fetal bovine serum, 1% sodium pyruvate, and 1% nonessential amino acids. IOSER cells were grown in 1:1 MCBD105 and Medium 199, HEPES, Bovine Pituitary Extract, Insulin, hEGF, hydrocortisone and 15% FBS. All tissue culture reagents were obtained from Sigma Aldrich (St Louis, Mo.). Cells were maintained in a $CO_2$ incubator at 37° C. and subcultured at 70% confluence. The cell lines consist of two from the NCI60 panel: IGR-OV1 (doubling time 31) and OVCAR-5 (doubling time 48.8). Several cell lines have mother/daughter relationships including A2008 and daughter C13; as well as A2780S/A2780CP.

A total of 123 advanced (stage III/IV) serous epithelial ovarian adenocarcinomas were obtained from patients treated at Duke University Medical Center and H. Lee Moffitt Cancer Center between 1988 and 2003. All ovarian cancers were obtained at initial cytoreductive surgery from patients who then received platinum-based adjuvant chemotherapy. Approximately 80/120 patients demonstrated a complete response (CR)—and 40/120 patients demonstrated an incomplete response (IR) to primary platinum-based therapy following surgery. All samples were subject to microarray gene expression analysis using Human GeneChips (Affymetrix, Santa Clara, Calif.).

To induce the development of platinum-resistance, the nine ovarian cancer cell lines were subjected to serial treatments with increasing dose cisplatin (Group A: 1 and 3 µg/mL, Group B: 2 and 4 µg/mL, and Group C: 3 and 5 µg/mL) using a protocol previously described by Hong et al (Antisense Bcl2 oligonucleotide in cisplatin-resistant bladder cancer cell lines. BJU Int. 2002 July; 90(1):113-7). For each of the 9 cell lines, three different dosage schedules were used: Schedule A—3 treatment/recovery cycles at 1 µg/mL, followed by 3 treatment/recovery cycles at 3 µg/mL; Schedule B—3 treatment/recovery cycles at 2 µg/mL, followed by 3 treatment/recovery cycles at 4 µg/mL; Schedule C—3 treatment/recovery cycles at 3 µg/mL, followed by 3 treatment/recovery cycles at 5 µg/mL. After each treatment, cells were allowed to recover before re-treatment. Gene expression analysis was performed prior to treatment, after 3 and 6 treatments. The experiment design and notations used for each treatment schedule are outlined in Table 1.

TABLE 1

Overview of experimental schema. Italics indicate RNA extraction after recovery from treatment.

| Initial Concentration | Treatment Number | Notation | | Final Concentration | Treatment Number | Notation |
|---|---|---|---|---|---|---|
| 1 µg/ml | 1 | 1.11 | | | | |
| | 2 | 1.22 | | | | |
| | 3 | *1.33* | plus 2 µg/ml = | 3 µg/ml | 1 | 3.14 |
| | | | | | 2 | 3.25 |
| | | | | | 3 | *3.36* |
| 2 µg/ml | 1 | 2.11 | | | | |
| | 2 | 2.22 | | | | |
| | 3 | *2.33* | plus 2 µg/ml = | 4 µg/ml | 1 | 4.14 |
| | | | | | 2 | 4.25 |
| | | | | | 3 | *4.36* |
| 3 µg/ml | 1 | 3.11 | | | | |
| | 2 | 3.22 | | | | |
| | 3 | *3.33* | plus 2 µg/ml = | 5 µg/ml | 1 | 5.14 |
| | | | | | 2 | 5.25 |
| | | | | | 3 | *5.36* |

Thus, for each of the 9 cell lines, 3 different starting doses of cisplatin were used with three different recovery cycles, such that a total of 162 treatment/recovery cycles were induced. Increasing platinum-resistance was confirmed by MTT cell proliferation assays prior to cisplatin treatment, and after 3 and 6 treatment/recovery cycles (for each treatment schedule).

MTT solution was produced by dissolving 3-(4,5-Dimethylthiazol-2-yl)-2,5-diphenyltetrazolium bromide (MTT; Sigma, St. Louis, Mo., USA) in phosphate-buffered saline (PBS; 5 mg/mL). Cells ($1 \times 10^3$) were incubated with 100 µL of culture medium for 48 h in 96-well plates, and 100 µL of MTT solution with RPMI media in a 1:10 concentration was added to each well. After 4 h of incubation, medium was decanted. 100 µL of acidified isopropanol was added to each well. The dye was directly quantified using a multiplate absorbency reader at 570-690 nm within 1 hour of addition of isopropanol. MTT assays were performed independently in triplicate per each experimental time point and means reported. For each cell line at each time-point for each schedule, an $IC_{50}$ was calculated using MTT assay, as well as a percent cell survival at a fixed cisplatin concentration (based upon the mid-point of the log-phase of the dose-response curve for each cell line at baseline), seen in Table 2.

TABLE 2

$IC_{50}$ values for the ovarian cancer cell lines experiments.

| Treated Cell Lines | 1.33 | 3.36 | 2.33 | 4.66 | 3.33 | 5.36 |
|---|---|---|---|---|---|---|
| IOSER | −0.3018 | −0.05819 | −0.3278 | −0.3687 | −0.6876 | 0.04473 |
| C13 | −0.125 | −0.4154 | −0.4353 | 0.5427 | −0.5361 | 0.1516 |
| OV2008 | −0.3752 | −0.07123 | −0.4324 | 0.3972 | −0.6905 | 0.03121 |
| IGROV1 | −0.1092 | −0.551 | −0.7421 | −0.3616 | −5.697 | −0.6600 |
| T8 | −1.379 | −0.05162 | −0.7823 | −0.6236 | −0.838 | −0.6746 |
| A2008 | −1.058 | −1.038 | −0.9188 | −0.8039 | −1.358 | −0.8943 |
| A2780S | −1.029 | −0.8731 | −0.9976 | −1.165 | −2.161 | −0.8829 |
| A2780CP | 0.01735 | 0.2333 | 0.3269 | 0.2137 | 0.4186 | 0.5259 |
| OVCAR5 | −0.6614 | −0.2545 | −0.5233 | −0.2349 | −0.9291 | −0.3127 |

Gene expression analyses were performed in parallel on a series of 63 cell line cisplatin treatment regimens or 132 primary advanced stage (III/IV) serous ovarian cancers, resected from patients who demonstrated either a complete or incomplete response to primary platinum-based chemotherapy. For both cell lines and patient samples, gene expression data was evaluated to identify genes and gene pathways associated with platinum resistance.

Prior to treatment (baseline), and at each dose level following treatment (3 and 6 treatment/recovery cycles) and cell recovery, RNA was extracted and genome-wide expression analysis performed using U133 plus 2.0 Affymetrix chips and cisplatin-resistance was quantified using MTT assay. In parallel, at each of these time-points, RNA was extracted and genome-wide expression analysis performed using U133 plus 2.0 Affymetrix chips. Array analysis was performed on 72 samples. Following recovery from each dose level, cells were evaluated for platinum-resistance using MTT proliferation assay, seen in Table 3. Cell line recovery was defined as the time taken for the cells to repopulate in a normal fashion (to reach 70% confluence in 48 hours). Cell line proliferation rate at 2 µg/mL was used as a measure of resistance.

TABLE 3

Cell population measurements for each experiment.

| Treated Cell Lines | Treatment Regimen | | | | | |
|---|---|---|---|---|---|---|
| | 1.33 | 3.36 | 2.33 | 4.36 | 3.33 | 5.36 |
| IOSER | 62 | 89 | 70 | 71 | 79 | 84 |
| C13 | 83 | 53 | 73 | 91 | 71 | 67 |
| OV2008 | 62 | 64.8 | 54 | 98 | 67 | 86 |
| IGROV1 | 69 | 68.3 | 48 | 69 | 55 | 58 |
| T8 | 42 | 68.4 | 64 | 69 | 67 | 62 |
| A2008 | 19 | 25.6 | 33 | 29 | 25 | 37 |
| A2780S | 26 | 30.5 | 39 | 87 | 64 | 72 |
| A2780CP | 84 | 100 | 100 | 83 | 91 | 98 |
| OVCAR5 | 49 | 66.5 | 41 | 69 | 47 | 63 |

Cancer biomarkers were identified, along with therapeutic response, using tissue microarrays. Response to therapy was evaluated from the medical record using standard criteria for patients with measurable disease, based upon WHO guidelines. CA-125 was used to classify responses only in the absence of a measurable lesion; CA-125 response criteria was based on established guidelines. A complete response (CR) was defined as a complete disappearance of all measurable and assessable disease or, in the absence of measurable lesions, a normalization of the CA-125 level following adjuvant therapy. An incomplete response (IR) included patients who demonstrated only a partial response (PR), had stable disease (SD), or demonstrated progressive disease (PD) during primary therapy. A partial response was considered a 50% or greater reduction in the product obtained from measurement of each bi-dimensional lesion for at least 4 weeks or a drop in the CA-125 by at least 50% for at least 4 weeks. Disease progression was defined as a 50% or greater increase in the product from any lesion documented within 8 weeks of initiation of therapy, the appearance of any new lesion within 8 weeks of initiation of therapy, or any increase in the CA-125 from baseline at initiation of therapy. Stable disease was defined as disease not meeting any of the above criteria.

Frozen tissue samples were embedded in OCT medium and sections were cut and mounted on slides. The slides were stained with hematoxylin and eosin to assure that the samples included greater than 70% tumor content. Approximately 30 mg of tissue was added to a chilled BioPulverizer H tube (Bio101). Lysis buffer from the Qiagen Rneasy Mini kit was added and the tissue homogenized for 20 seconds in a Mini-Beadbeater (Biospec Products). Tubes were spun briefly to pellet the garnet mixture and reduce foam. The lysate was transferred to a new 1.5 ml tube using a syringe and 21 gauge needle, followed by passage through the needle 10 times to shear genomic DNA. Total RNA was extracted from primary tumor samples and cell lines at baseline and at each time point (following 3 and 6 treatment/recovery cycles) using the Qiahredder an Qiagen RNeasy Mini kit. Two extractions were performed for each sample and the total RNA pooled at the end of the RNeasy protocol, followed by a precipitation step to reduce volume. Quality of the RNA was checked by an Agilent 2100 Bioanalyzer. The targets for Affymetrix DNA microarray analysis were prepared according to the manufacturer's instructions. Biotin-labeled cRNA, produced by in vitro transcription, was fragmented and hybridized to the Affymetrix GeneChip arrays at 45° C. for 16 hr and then washed and stained using the GeneChip Fluidics. The arrays were scanned by a GeneArray Scanner and patterns of hybridization detected as light emitted from the fluorescent reporter groups incorporated into the target and hybridized to oligonucleotide probes. All analyses were performed in a MIAME (minimal information about a microarray experiment)-compliant fashion, as defined in the guidelines established by MGED (MGED, hosted at EBI, Hinxton, UK).

Linear regression was performed to identify genes with expression changes associated with increasing numbers of cisplatin treatments, and increasing cisplatin resistance as measured by $IC_{50}$ or cell survival at a fixed concentration. In parallel, patient mRNA data was compared between patients that demonstrated a CR versus IR. Genes associated with platinum resistance in both cell line and patient samples were analyzed using GeneGo's MetaCore software (GeneGO, Inc.; St. Joseph, Mich.) to identify molecular pathways that are represented by genes associated with platinum resistance in both patient and cell line samples.

Data pre-processing prior to the formal statistical analysis involved standard processes of normalization, expression intensity estimation and screening for genes showing reasonable variation across samples. For both training and validation sample sets the expression intensities for all genes across the samples were estimated using Robust Microarray Analysis (RMA), with probe-level quantile normalization, as implemented in the Bioconductor software suite (Bioconductor 2.3, Bioconductor, Seattle, Wash.). The resulting RMA expression intensity estimates were then screened to identify probe sets showing some evidence of more than trivial variation across samples above noise levels. Specifically, genes whose RMA levels vary less than 1.5 fold across the samples, or whose media value was less than 7.5 on the log 2 scale were removed.

Cell line microarray data was then analyzed using a linear regression to model increasing cisplatin resistance from changes in gene expression with factors including gene expression, number of treatments, and increasing dose level. ANOVA was used to analyze factor effects. Pathway analysis was performed using GeneGo's MetaCore software (GeneGO, Inc.; St. Joseph, Mich.). The results indicate that phospho-BAD protein expression is significantly higher for IR (platinum resistant) than CR (platinum sensitive) patient samples and. This change in phosphor-BAD is further increased as ovarian cancer cell lines became more resistant to platinum with serial in-vitro treatments, indicating a positive correlation between cellular resistance to platinum therapy and BAD phosphorylation levels.

Example 2

Immunohistochemistry of Amino Acid Residues Function as Biomarkers for Cancer

Genes found to be associated with platinum resistance in patient and cell line samples were further studied using immunohistochemistry (IHC) to evaluate the effect of differential mRNA expression on protein levels. Immunohistochemical (IHC) analysis of paraffin-embedded samples was used to analyze the pathology of diseased tissues.

Determining the molecular pathology of a tumor in order to identify relevant biomarkers of outcome may be accomplished using the methods of the present invention with IHC analysis of paraffin-embedded tissues. IHC analysis of patient tissue samples with phospho-specific antibodies to downstream signaling molecules may be used, for example, to prescreen patients for inclusion in a clinical trial, to follow patients during treatment and to detect resistance to the targeted therapeutic.

Figure 3:
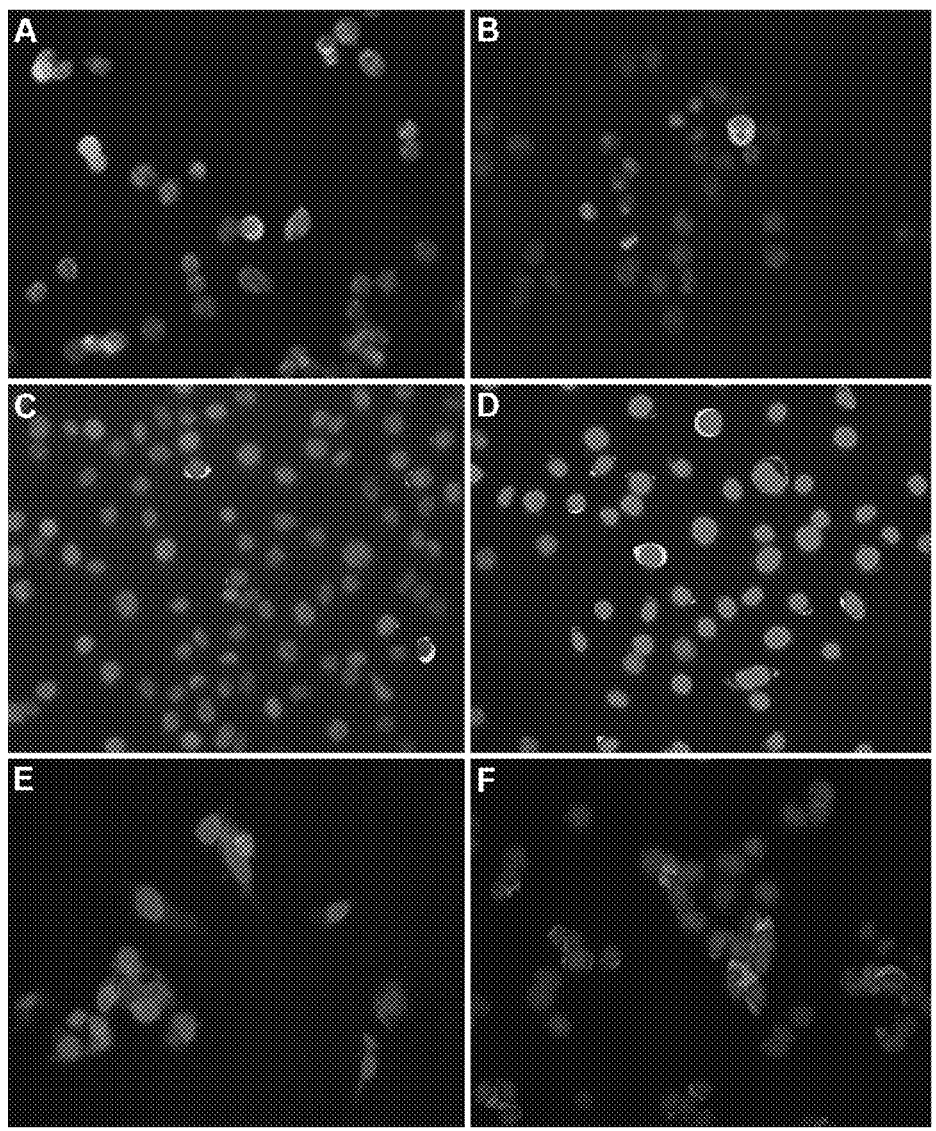
FIG. 3(A) depicts a photomicrograph of the cisplatin sensitive cell line A2780s, treated by a single administration of cisplatin at 1 µg/µl. Light gray cells indicate positive staining for BAD 155.
FIG. 3(B) depicts a photomicrograph of the cisplatin resistant cell line A2780 cp, treated by a single administration of cisplatin at 1 µg/µl. Light gray cells indicate positive staining for BAD 155.
FIG. 3(C) depicts a photomicrograph of the cisplatin sensitive cell line A2008, treated by a three separate treatments with cisplatin at 3 µg/µl, followed by an additional three separate treatments at 5 µg/µl. Light gray cells indicate positive staining for phosphorated BAD 155.
FIG. 3(D) depicts a photomicrograph of the cisplatin resistant cell line C13, treated by a three separate treatments with cisplatin at 3 µg/µl, followed by an additional three separate treatments at 5 µg/µl. Light gray cells indicate positive staining for phosphorated BAD 155.
FIG. 3(E) depicts a photomicrograph of the cisplatin sensitive cell line A2780s, treated by a three separate treatments with cisplatin at 3 µg/µl, followed by an additional three separate treatments at 5 µg/µl. Light gray signal around cells indicate positive staining for PP1MA (alternative name PP2C).
FIG. 3(F) depicts a photomicrograph of the cisplatin resistant cell line A2780 cp, treated by a three separate treatments with cisplatin at 3 µg/µl, followed by an additional three separate treatments at 5 µg/µl. Light gray cells indicate positive staining for PP1MA (alternative name PP2C).

BAD is phosphorylated at its Serine 155 residue, as seen in FIG. 3(A)-(F) and FIGS. 4(A) and (B) as compared to FIGS. 3(E) and (F). Tissue samples of ovarian tissue culture or ovarian serous adenocarcinoma were collected from patients. The cisplatin response was confirmed for the samples, and an exemplary serous adenocarcinoma with incomplete response to cisplatin, seen in FIGS. 4(A) and (C), and serous adenocarcinoma with complete response to cisplatin, seen in FIGS. 4(B) and (D), were analyzed. For harvesting, the cells were washed, pelleted, and fixed and embedded in OCT medium and sections were cut and mounted on slides. The slides were stained with hematoxylin and eosin to assure that the samples included greater than 70% tumor content. Cellular slices were cut at 2-4 μm from the OCT medium blocks using a microtome and placed on glass slides. The sections were then dried for about 30 minutes at room temperature and fixed in acetone for 1-2 minutes at room temperature. After the samples air dried for about 10 minute, the sections were blocked in 5% goat serum for 1 hour. The cell slides were then stained with phospho-BAD ser155 antibody (Cell Signaling Technology, Inc.) for 2 hours at room temperature or overnight at 4° C. After 3 washes in Tris-saline, the slides were then probed with a fluorescent secondary antibody (Invitrogen Corp., Carlsbad, Calif.). Positive staining for antibody staining was scored (positive-negative) based upon staining intensity, number of cells stained and correct localization of stain. The frequencies of scores were tabulated and the Chi-Squared tests of significance were calculated using standard statistical methods.

In the initial phase of this analysis, antibodies to total BAD, phosphorylated BAD, non-phosphorylated BAD, and PP2C, were used with cell lines after one treatment with cisplatin, and after 6 treatments. In parallel, total BAD, phosphorylated BAD, non-phosphorylated BAD, and PP2C was measured in a set of 40 patient samples (20 IR, 20 CR).

Ovarian cell cultures were the characterized for BAD status, and BAD status correlated to cisplatin resistance or sensitivity. FIGS. 3(A) and (B) are a paired ovarian cancer cell line A2780s (cisplatin sensitive) and A2780 cp (cisplatin resistant). A2780 cells were treated once with 1 μg/μl, followed by staining similar to the protocol discussed above. BAD 155 positive signal is seen as medium gray on the images. In FIGS. 3(C) and (D), A2008 (cisplatin sensitive) and C13 cisplatin resistant) cells were treated with 3 μg/μl cisplatin, followed by 3 administrations of 5 μg/μl. The cells were then stained with phospho-BAD ser155 antibody (Cell Signaling Technology, Inc.) PP2C (also known as PP1MA) is a serine/threonine specific protein phosphatase implicated in the negative control of cell growth and division. It is thought to target Raf, MEK, and Akt. A2780s cells (cisplatin sensitive) and A2780 cp (cisplatin resistant cell line) were treated by cisplatin at 3 μg/μl 3 times, followed by 3 administration of cisplatin at 5 μg/μl. PP2C staining was then conducted, noting the PP2C staining is a light signal as seen in FIGS. 3(E) and (F). The results of the immunohistochemical study of the ovarian tumor sections were then analyzed for significant correlations between phosphorylation states of BAD and pathological indices including therapeutic resistance, seen in FIG. 3(A)-(F). Though total levels of BAD are similar between cisplatin resistant and sensitive cells. However, as seen in the cisplatin sensitive cells of FIG. 3(C) and cisplatin resistant cells of FIGS. 3(C), phospho-BAD ser155 antibody-stained protein appears more prevalent in the cisplatin resistant cells. In conjunction with BAD phosphorylated at its ser155, PP2C levels are elevated in cisplatin resistant cells.

Figure 4:
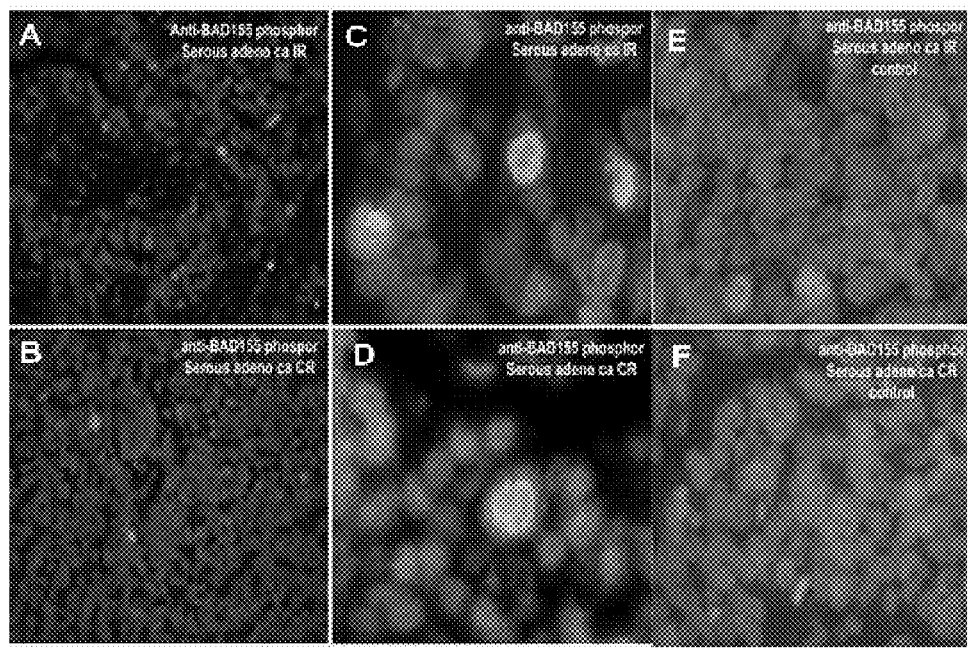
FIG. 4(A) depicts a photomicrograph of phospho-BAD protein expression in platinum resistant cells.
FIG. 4(B) depicts a photomicrograph of phospho-BAD protein expression in platinum resistant cells.
FIG. 4(C) depicts a magnified photomicrograph of phospho-BAD protein expression in platinum resistant cells of FIG. 3(A).
FIG. 4(D) depicts a magnified photomicrograph of phospho-BAD protein expression in platinum resistant cells of FIG. 3(B).
FIG. 4(E) depicts a photomicrograph of phospho-BAD protein expression in platinum sensitive cells.
FIG. 4(F) depicts a photomicrograph of phospho-BAD protein expression in platinum sensitive cells.

FIG. 4(A) shows cells after early cisplatin treatments at 1.33, whereas FIG. 4(B) shows cells after late cisplatin treatment at 3.33. As cells attain higher cisplatin resistance, seen in FIGS. 4(A) and (B), BAD Ser155 phosphorylation increases overall. Moreover, some cells appear to greatly phosphorylate BAD Ser 155 during cisplatin resistance, seen in FIGS. 4(C) and (D). These results indicate the usefulness of the method of the invention in profiling treatment resistance status, as well as cellular signaling events, in IHC embedded cells or tissues.

Results indicate phosphorylation of Serine 155 of BAD is directly associated with platinum therapeutic resistance, with phospho-BAD protein expression increasing as ovarian cancer cell lines became more resistant to platinum with serial in-vitro treatments. Further, the immunohistochemical results show phospho-BAD protein expression was higher in platinum resistant cell lines and patient samples versus platinum sensitive cells and patient samples. Based upon this data, platinum resistance may be predicted by monitoring BAD Serine 155 phosphorylation. These results further indicate the power of an IHC analysis using panels of phospho-specific antibodies to provide new prognostic information for cancer patients.

Example 3

Targeted Inhibition of AKT in BAD Ser155 Phosphorylated Cells

To further evaluate the relevance of BAD phosphorylation status on cisplatin sensitivity, the ovarian cancer cell lines—IGROV1, IGROV1 (5.3.6), OvCAR4, SKOV3—were subjected to treatment with the AKT inhibitor triciribine, both in the presence and absence of cisplatin. Cells were incubated at 37° C. in $CO_2$, followed by administration of 3 doses of cisplatin, as discussed in Example 1.

Overexpression/activation and/or amplification of AKT 1 and AKT2 in human ovarian and pancreatic cancer has been shown (Cheng, J. Q., and Nicosia, S. V. AKT signal transduction pathway in oncogenesis. In Schwab D, Editor, Encyclopedic Reference of Cancer. Berlin Heidelberg and New York: Springer; 2001. pp 35-7). Cells were treated with 30 M triciribine (TCN), 25 M cisplatin, or both 30 TCN and 25 M cisplatin, and analyzed over a 72 hour period. TCN showed a decrease in tumor cell viability throughout all tested cells, even the cisplatin resistant cells, such as SKOV3. AKT inhibition by triciribine was confirmed over a 72 hour period, showing a time-dependent AKT reduction by all cell lines treated with triciribine or cisplatin and triciribine, as seen in FIGS. 5-8. Interestingly, the co-treatment of triciribine and cisplatin considerably depressed AKT levels below levels of triciribine. Treatment of cell lines with TCN inhibited AKT expression in OVCAR4 and SKOV3 tumor cells by up to 90%. After confirming AKT protein levels, cell survival was investigated by MTS assay, seen in FIGS. 9-13. MTS (3-(4, 5-dimethylthiazol-2-yl)-5-(3-carboxymethoxyphenyl)-2-(4-sulfophenyl)-2H-tetrazolium) was dissolved in phenazine methosulfate (PMS), and added to each cell culture in 100 μL of RPMI media in a 1:10 concentration. The cell cultures were incubated for 4 h, the medium removed and the cells fixed with 100 μL of acidified isopropanol to each 96-plate well. The dye was directly quantified using a multiplate absorbency reader at 490-500 nm in phosphate-buffered saline.

Figure 5:
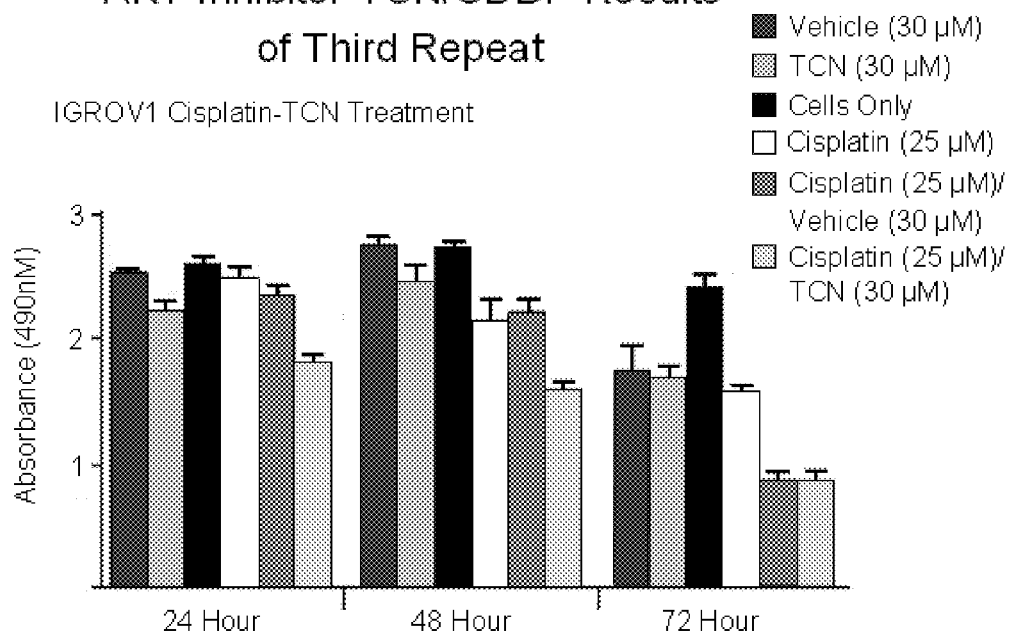
FIG. 5 depicts AKT expression in cisplatin resistant and sensitive IG ROV1 ovarian carcinoma cell lines. Protein levels were analyzed after an initial anticancer treatment with cisplatin, a second treatment with cisplatin, and a third treatment with cisplatin.
Figure 6:
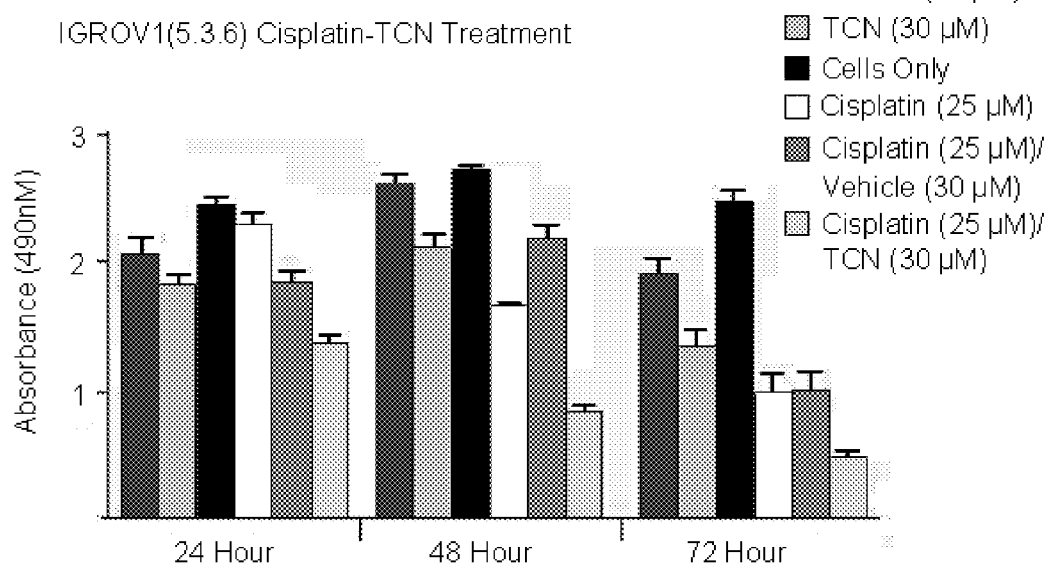
FIG. 6 depicts AKT expression in cisplatin resistant and sensitive IG ROV1 (5.3.6) ovarian carcinoma cell lines. Protein levels were analyzed after an initial anticancer treatment with cisplatin, a second treatment with cisplatin, and a third treatment with cisplatin.
Figure 7:
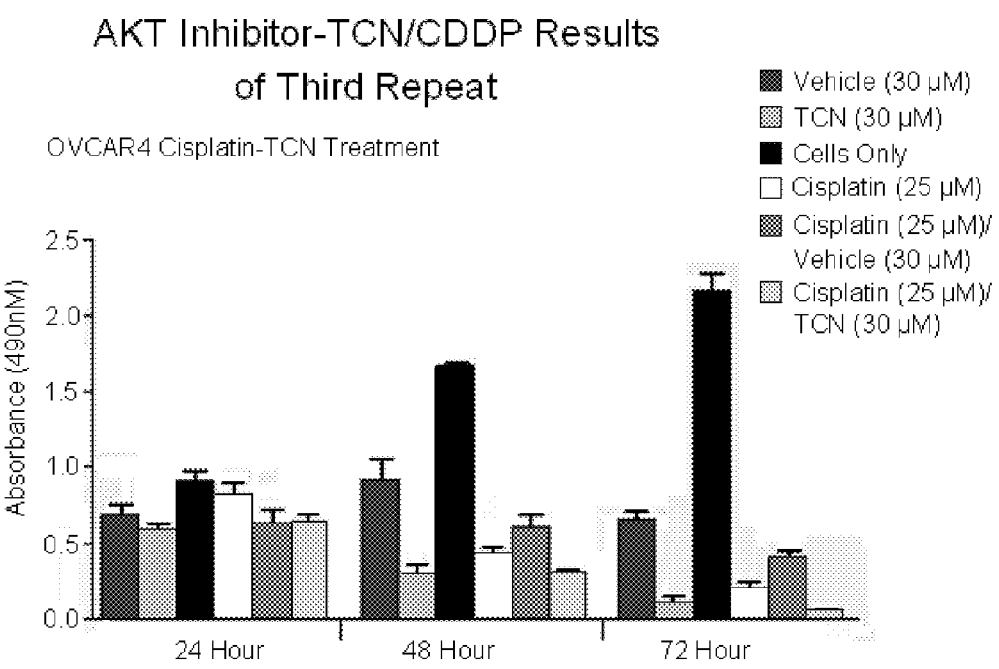
FIG. 7 depicts AKT expression in cisplatin resistant and sensitive OVCAR4 ovarian carcinoma cell lines. Protein levels were analyzed after an initial anticancer treatment with cisplatin, a second treatment with cisplatin, and a third treatment with cisplatin.
Figure 8:
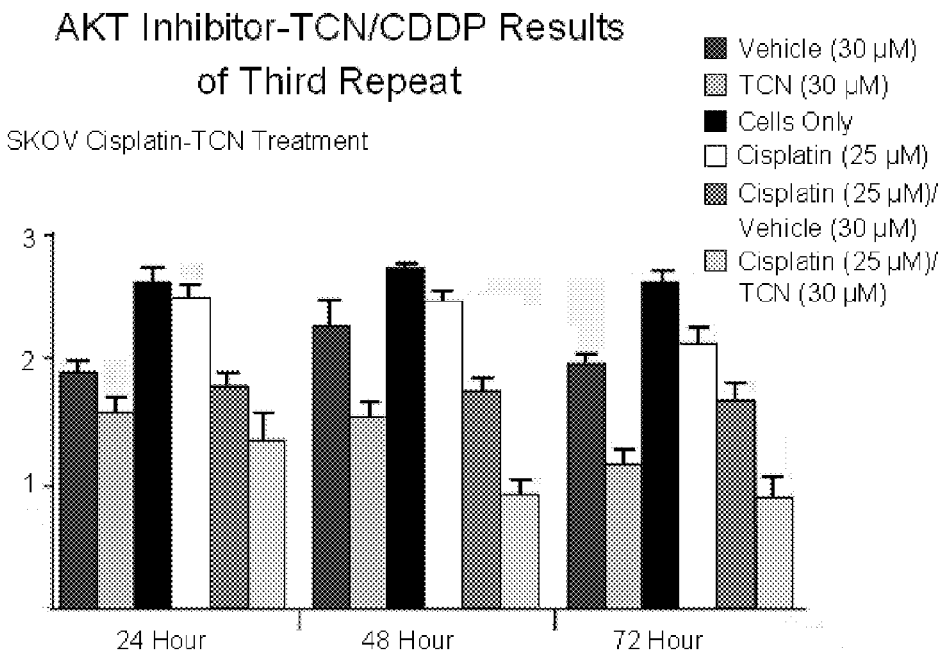
FIG. 8 depicts AKT expression in cisplatin resistant and sensitive SKOV3 ovarian adenocarcinoma cell lines. Protein levels were analyzed after an initial anticancer treatment with cisplatin, a second treatment with cisplatin, and a third treatment with cisplatin.
Figure 9:
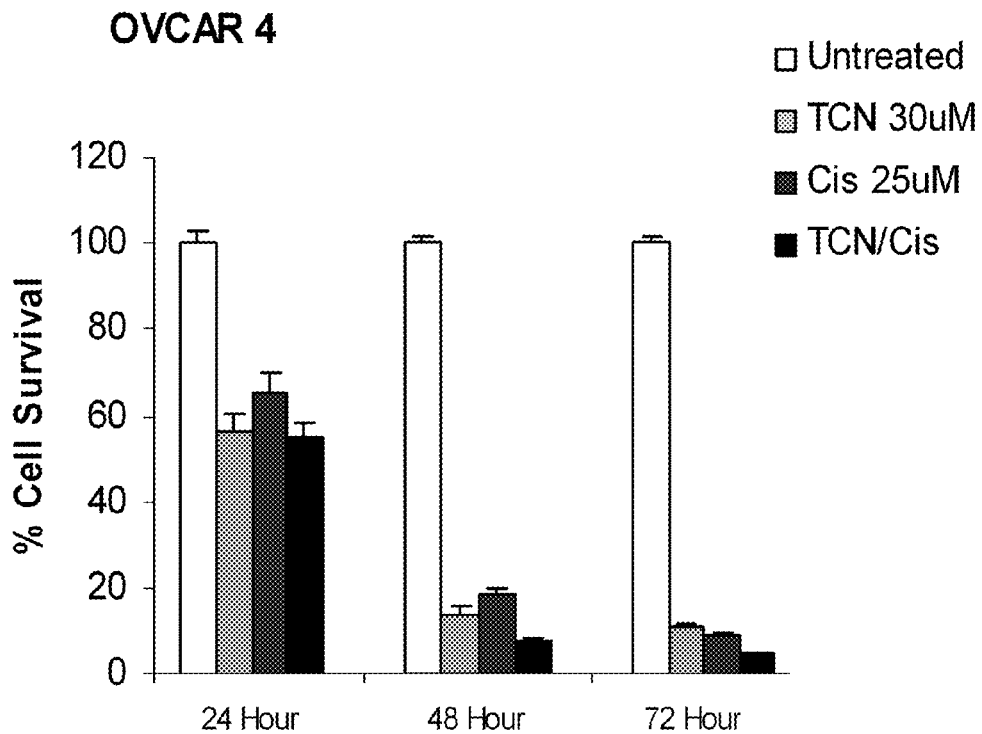
FIG. 9 depicts cell survival in OVCAR 4 ovarian carcinoma cell lines. Survival was determined by MTS assay after an initial anticancer treatment with cisplatin, a second treatment with cisplatin, and a third treatment with cisplatin.
Figure 10:
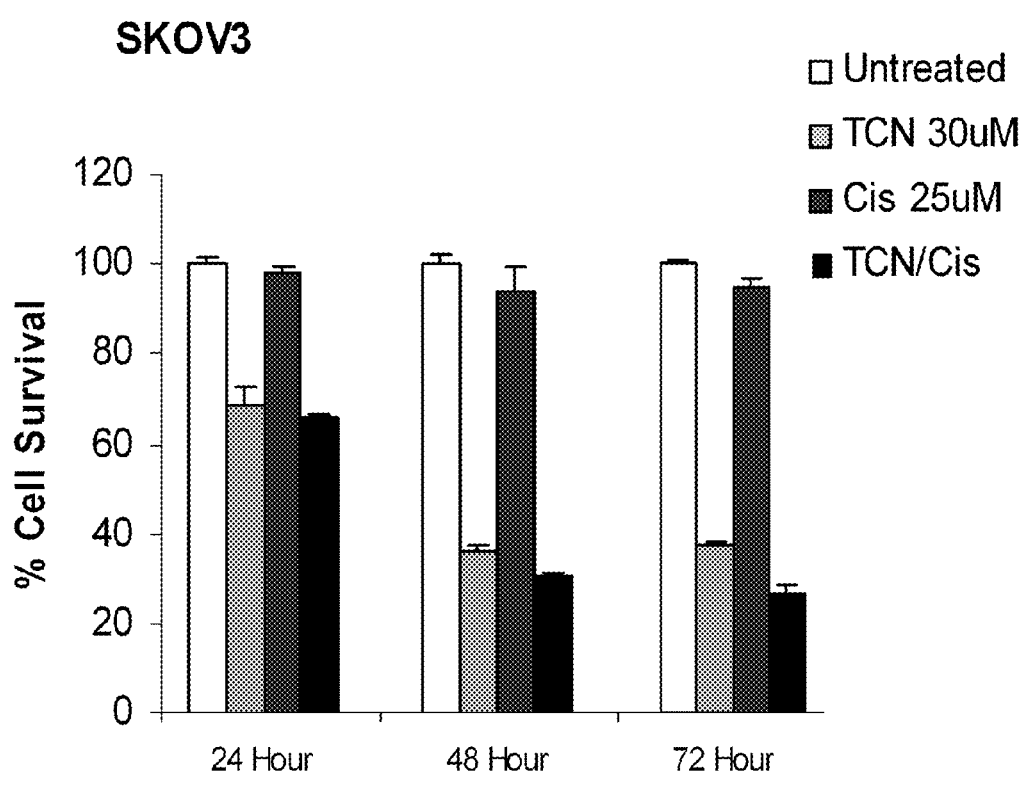
FIG. 10 depicts cell survival in SKOV3 ovarian adenocarcinoma cell lines. Survival was determined by MTS assay after an initial anticancer treatment with cisplatin, a second treatment with cisplatin, and a third treatment with cisplatin.
Figure 11:
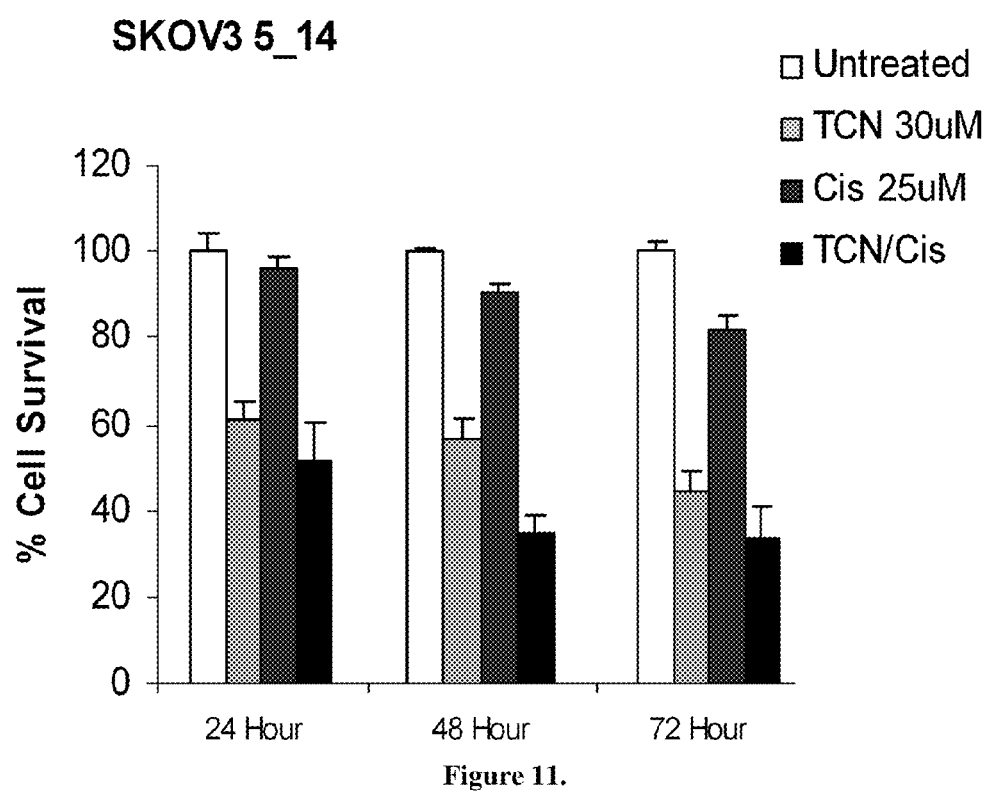
FIG. 11 depicts cell survival in SKOV3 (5_14) ovarian adenocarcinoma cell lines. Survival was determined by MTS assay after an initial anticancer treatment with cisplatin, a second treatment with cisplatin, and a third treatment with cisplatin.
Figure 12:
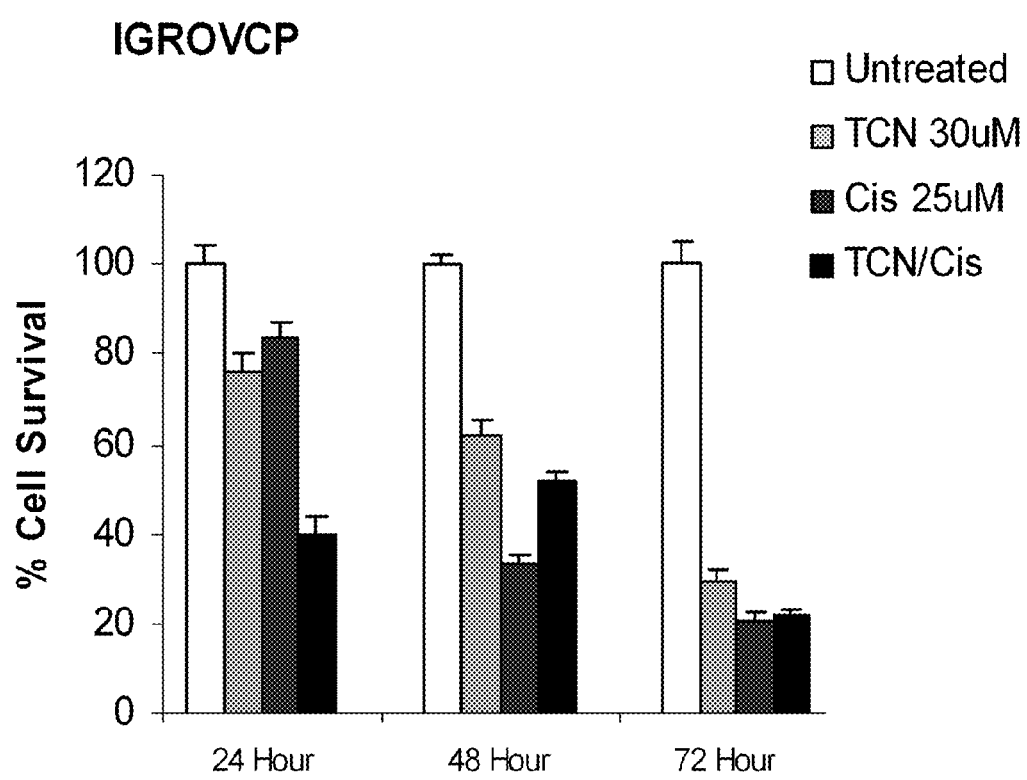
FIG. 12 depicts cell survival in IG ROV1 CP ovarian carcinoma cell lines. Survival was determined by MTS assay after an initial anticancer treatment with cisplatin, a second treatment with cisplatin, and a third treatment with cisplatin.
Figure 13:
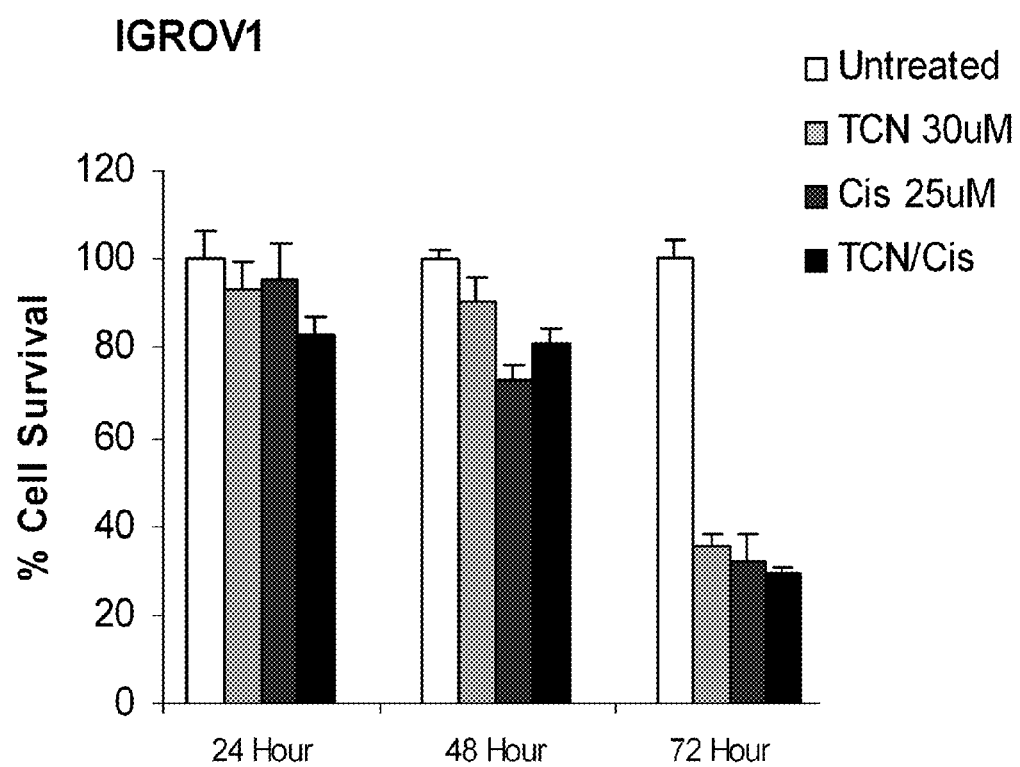
FIG. 13 depicts cell survival in IG ROV1 ovarian carcinoma cell lines. Survival was determined by MTS assay after an initial anticancer treatment with cisplatin, a second treatment with cisplatin, and a third treatment with cisplatin.

The administration of triciribine and cisplatin further resulted in an overall decrease in cell survival, which was expected since tumor xenografts with elevated Akt were significantly inhibited by intratumoral injection of adenovirus of dominant negative Akt (Jetzt, A, et al. Cancer Res, 63: 697-706, 2003). Further, inhibition of AKT increased ovarian cancer cell platinum sensitivity. As seen in FIGS. 5 and 6, treatment with vehicle did not significantly alter AKT expression levels from no treatment (cells only) in the first two treatment cycles, but did impact OVCAR and SKOV3 cell lines slightly, seen in FIGS. 7 and 8. Taken together, these results indicate that indirect manipulation of BAD phosphorylation status influences cisplatin sensitivity. The BAD pathway, or at least BAD phosphorylation, appears to represent a therapeutic target to increase platinum sensitivity.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of phosphorylation-based diagnostic for tumor prediction, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention that, as a matter of language, might be said to fall therebetween.

What is claimed is:

1. A method for determining cancer treatment sensitivity, comprising:
   providing a cellular sample from an ovary of an ovarian cancer patient prior to platinum-based chemotherapy treatment;
   forming a plurality of cell cultures from the cellular sample;
   contacting the cell cultures with a plurality of predetermined amounts of the platinum-based chemotherapy treatment at more than one timepoint;
   evaluating the phosphorylation status of BCL-2 Associated Death Promoter in the cell cultures, comprising:
      isolating BCL-2 Associated Death protein from the cell cultures;
      contacting the BCL-2 Associated Death protein from the cell cultures with at least one antibody, wherein the at least one antibody is anti-phospho-BAD ser 155; and
      comparing the phosphorylation status of the ser155 amino acid residue on BCL-2 Associated Death Promoter in the cell cultures to a phosphorylation status of the ser155 amino acid residue on BCL-2 Associated Death Promoter on a platinum-based chemotherapy sensitive sample control;
   wherein an elevated phosphorylation status of the BCL-2 Associated Death Promoter is indicative of platinum-based chemotherapy resistivity.

2. The method of claim 1, wherein the cancer treatment is cisplatin.

3. The method of claim 1, wherein the cellular samples are further collected by biopsies, ductal lavages, or fine needle aspirants.

4. The method of claim 1, wherein the phosphorylation status of BCL-2 Associated Death Promoter is evaluated by a testing method selected from the group consisting of immunohistochemical, immunofluorescent, reverse-phase array, flow cytometric analysis, and tissue microarray.

5. The method of claim 4, wherein the immunohistochemical testing method is performed comprising the steps
   fixing and embedding cells from the cellular sample;
   cutting sections from the embedded cells; and
   staining the sections with antibodies against the at least one amino acid residue on BCL-2 Associated Death Promoter.

6. The method of claim 1, further comprising evaluating the RNA expression status of PP2C, wherein the RNA expression is evaluated by
   contacting protein, RNA, or cDNA from the cellular sample prior to platinum-based chemotherapy treatment with an antibody directed to PP2C; and
   comparing the expression levels of the PP2C in the cellular sample to an expression levels of PP2C on a platinum-based chemotherapy-sensitive sample control;
   wherein an elevated expression level of PP2C is indicative of platinum-based chemotherapy resistivity.

7. A method for determining cisplatin treatment sensitivity, comprising:
   providing a cellular sample from an ovary of an ovarian cancer patient prior to cisplatin chemotherapy treatment;
   forming a plurality of cell cultures from the cellular sample;
   contacting the cell cultures with a plurality of predetermined amounts of the platinum-based chemotherapy treatment at more than one timepoint;
   evaluating the phosphorylation status of BCL-2 Associated Death Promoter in the cell cultures using a testing method selected from the group consisting of immunohistochemical, immunofluorescent, reverse-phase array, flow cytometric analysis, and tissue microarray;
   wherein the evaluating is performed by the steps comprising
      isolating BCL-2 Associated Death protein from the cell cultures;
      contacting the BCL-2 Associated Death protein with at least one antibody, wherein the at least one antibody is anti-phospho-BAD155; and
   comparing the phosphorylation status of the ser155 amino acid residue on BCL-2 Associated Death Promoter in the cell cultures to a phosphorylation status of the ser155 amino acid residue on BCL-2 Associated Death Promoter on a cisplatin-sensitive sample control;
   wherein an elevated phosphorylation status of the BCL-2 Associated Death Promoter is indicative of cisplatin resistivity.

8. The method of claim 7, wherein the cellular samples are further collected by biopsies, ductal lavages, or fine needle aspirants.

9. The method of claim 7, further comprising evaluating the RNA expression status of PP2C, wherein the RNA expression is evaluated by
   contacting protein, RNA, or cDNA from the cellular sample prior to platinum-based chemotherapy treatment with an antibody directed to PP2C; and
   comparing the expression levels of the PP2C in the cellular sample to an expression levels of PP2C on a cisplatin-sensitive sample control;
   wherein an elevated expression level of PP2C is indicative of cisplatin chemotherapy resistivity.

* * * * *